United States Patent [19]

Kalwaitis

[11] 4,294,124

[45] Oct. 13, 1981

[54] APPARATUS FOR EXTRACTION OF MATERIALS FROM OPERATING PRESSURIZED VESSELS

[75] Inventor: George V. Kalwaitis, Gulf Breeze, Fla.

[73] Assignee: Air Products and Chemicals, Inc., Allentown, Pa.

[21] Appl. No.: 139,073

[22] Filed: Apr. 10, 1980

[51] Int. Cl.³ .............................................. G01N 1/10
[52] U.S. Cl. ................................................. 73/863.85
[58] Field of Search .......... 73/421 A, 422 R, 422 TC, 73/86, 861.65, 861.67, 421.5 A

[56] References Cited

U.S. PATENT DOCUMENTS 2,119,288  5/1938  Raymond ........................... 73/422 R
3,115,782 12/1963  Echtler ............................. 73/422 TC
3,276,264 10/1966  Banks ............................... 73/422 R
4,054,060 10/1977  Veno et al. ...................... 73/421.5 A

*Primary Examiner*—S. Clement Swisher
*Attorney, Agent, or Firm*—Douglas G. Glantz; E. Eugene Innis

[57] ABSTRACT

Apparatus is disclosed for withdrawing and collecting samples from a pressure vessel without disturbing either the reaction pressure contained within the vessel or the physical conditions of the sample which is extracted. A tubular probe having a perforated end is contained in a sealable second tube capable of attachment to an operating reaction pressure vessel. The probe is capable of sliding into the pressure vessel and withdrawing a sample of material from the pressure vessel without disturbing the reaction contained therein. The probe is capable of withdrawing the sample material and collecting it in the sealable second tube, which can be removed and carried away to analyze the samples.

8 Claims, 2 Drawing Figures

APPARATUS FOR EXTRACTION OF MATERIALS FROM OPERATING PRESSURIZED VESSELS

BACKGROUND OF THE INVENTION

1. Field of the Invention

This invention relates to a sample collecting apparatus capable of withdrawing and collecting samples from a pressure vessel without disturbing a reaction contained in the pressure vessel and without disturbing the physical conditions of the sample withdrawn and collected.

2. Description of the Prior Art

Numerous devices are known for withdrawing sample materials from zone volumes having a different pressure. German Patentschrift No. 185,004 discloses a sampling device for withdrawing solid materials from a reactor. However, the German device makes no provision for withdrawing and collecting the sample at the conditions of the reactor.

Kalka et al, U.S. Pat. No. 4,056,981, discloses a double valving device for withdrawing a sample from a pressure vessel. Kalka et al, however, withdraws the sample by means of a suction device which thereby destroys the integrity of the physical conditions of the sample.

Norwegian Pat. No. 80,078 discloses a device for removing samples from a cellulose digestor, and which is permanently attached to the cellulose reactor. Not shown are means for removing the sample collection tube while maintaining the integrity of the physical conditions of the sample contained therein.

It is an object of this invention to provide for a perforated tube in a sampling device capable of extending into a reactor and collecting a sample material at an equilibrium with the contents of the reactor before the probe is withdrawn.

It is a further object of this invention to provide for a device to obtain accurate samples without disturbing the reaction from which sampling is desired.

It is a further object of this invention to provide for a tube containing the withdrawn sample material at equilibrium with the contents of the reactor and to maintain the physical conditions of the sample in a sealed second tube capable of removal for analysis of the sample at a remote location.

SUMMARY OF THE INVENTION

An apparatus is provided for withdrawing and collecting sample materials from a reaction mixture in a pressure vessel, during the ongoing reaction and while the process within the pressure vessel is operating, without disturbing the ongoing reaction and with maintaining the physical condition of said sample material which is withdrawn and collected. The novel sampling apparatus includes a sealable probe comprising concentric tubes, one within the other, the inner tube having a perforated end for receiving samples and slidably connected to the outer tube. The sealable probe is capable of being removably attached to a pressure vessel having an aperture and a valve sealing the aperture. The invention also provides means for guiding the perforated inner tube into and out of the pressure vessel at predetermined distances.

DETAILED DESCRIPTION

The apparatus of the invention provides for the extraction of sample materials, which can be of any phase, liquid, gaseous, or solid, from an operating reactor, while the reactor is under operating pressure and without disturbing the reaction contained in the reactor. The probe can withdraw and collect sample materials at an equilibrium with materials in the reactor in a sealable collection tube, which then can be removed from the pressure vessel and carried away to analyze the samples at a remote location. The sampling apparatus is capable of maintaining the physical conditions of the sample materials, which capability requires the ability to maintain the physical conditions of the ongoing reaction in the reactor. The sampling apparatus can contain typical reaction conditions contained in the reactor, e.g., pressures from about 0.0001–300 psia and temperatures to at least 800° F.

The apparatus provides a means for sampling materials and for maintaining operating conditions in the reactor in order to obtain factual data of what is occurring inside the reactor without introducing an extraneous influence which can alter the reaction. Similarly the integrity is maintained of the physical conditions of the sample material, which can be a reaction component and product or secondary material, such as a catalyst, collected in the probe to provide for precision qualitative or quantitative analyses of the sample at a remote location other than at or near the reactor.

Figure 1:
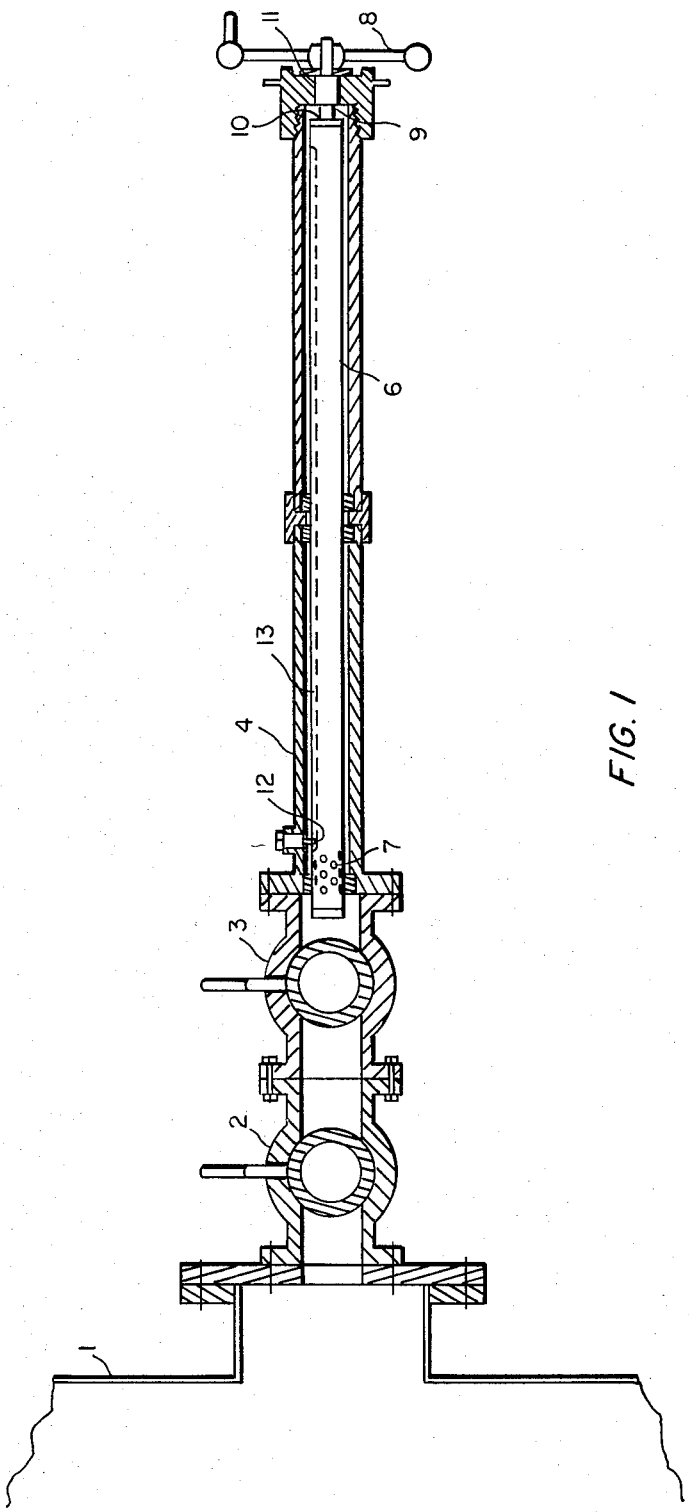
FIG. 1 illustrates the apparatus of the invention when the perforated tube end is withdrawn into the sealable probe.

Referring to FIG. 1, pressure vessel 1 containing a reaction mixture at either an elevated or evacuated pressure has attached to it ball valve 2 which is in its sealed position so that ongoing reaction within reaction vessel 1 can continue undisturbed. Ball valve 3 is removably attached to ball valve 2 by means of nuts and bolts or the like which may easily be connected and disconnected. Valves 2 and 3 can be gate valves or plug valves or similar valve or combinations thereof capable of containing the pressure in vessel 1. Ball valve 3 is attached to outer tube 4 which is sealed at the end opposite to ball valve 3. Inner tube 6 is contained coaxially within tube 4 and has perforations 7 at the end nearest ball valve 3. Tube 6 is connected to crank 8 by threaded rod 9 through sealed end 11 containing seals which can withstand the pressures inside pressure vessel 1. Threaded rod 9 extends into tube 6 through a threaded bore 10 in the end wall of tube 6. Threaded bore 10 is inside-threaded to suit the outside threads of rod 9. Turning crank 8 rotates rod 9 in threaded bore 10 thereby linearly moving tube 6 along the longitudinal axis of tube 4 in a direction dependent on the direction crank 8 is turned. Key 12 is mechanically fastened pressure tight in the wall of tube 4 and projects internally within tube 4 into keyway 13 of tube 6 to provide a guiding means for sliding tube 6 within tube 4. Key 12 allows tube 6 to move only linearly along the longitudinal axis of tube 4 on threaded rod 9 when crank 8 is turned.

Key 12 can be located in the wall of tube 4 so as to allow tube 6 to travel only a pre-determined distance, thereby withdrawing and collecting samples at an equilibrium with materials at a known distance from the wall of pressure vessel 1. A plurality of pre-determined distances are provided by plugged bores 14 which when not used for Key 12 are filled with plugs 15 to maintain the sealed condition of tube 4.

Keyway 13 alternatively may be located as part of outer tube 4 if Key 12 is made a part of and fixed on slideable tube 6.

The seals in sealed end 11 can be conventional stem type packing which can withstand reaction pressures at least to 300 psi and temperatures up to 800° F. and which is chemically resistant. Examples of suitable packing materials include graphite, asbestos, and stainless steel.

Figure 2:
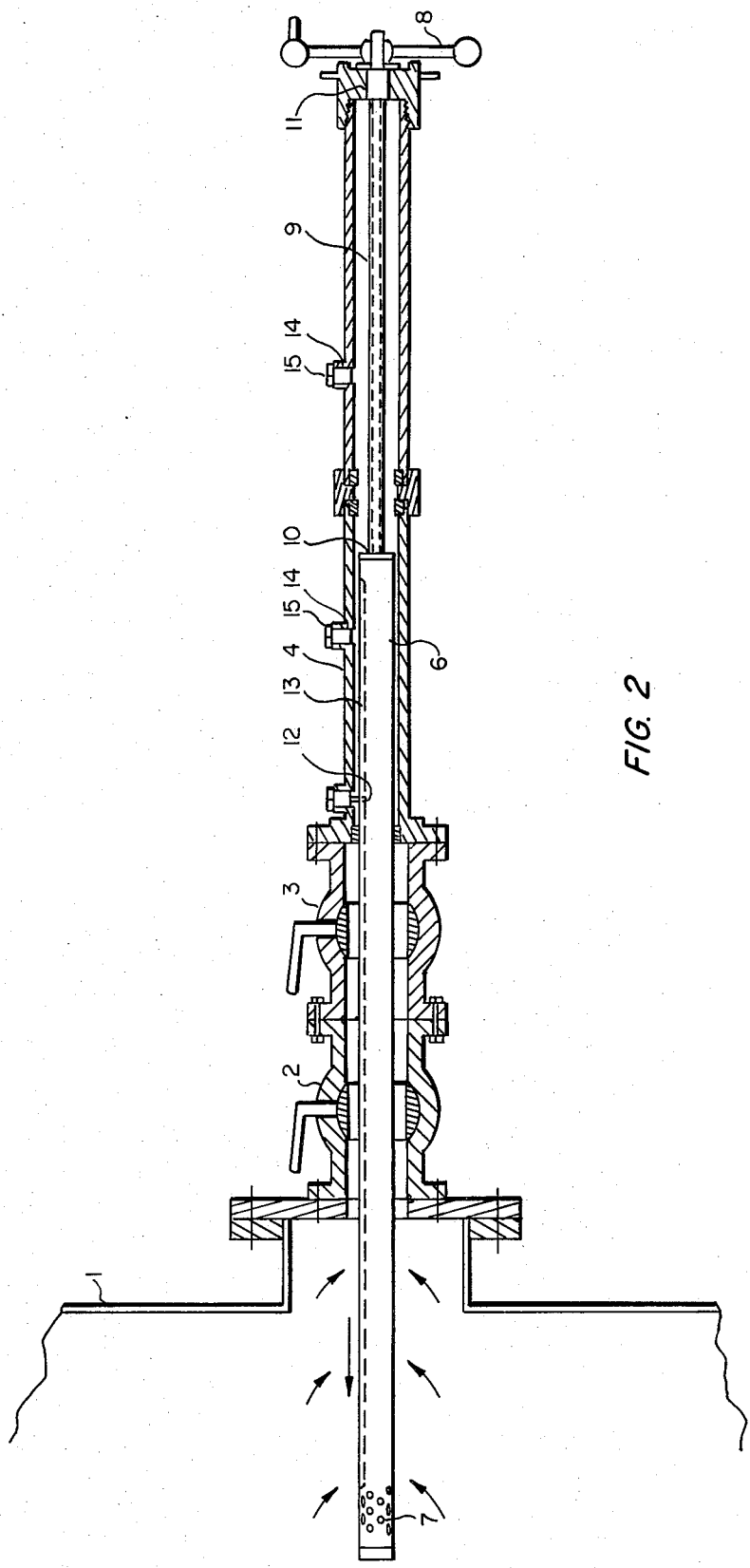
FIG. 2 illustrates the apparatus of the invention when the perforated tube of the probe is extended into the pressure reactor for collecting sample material at reaction equilibrium.

Referring to FIG. 2, ball valves 2 and 3 are opened and crank 8 has extended tube 6 into pressure reactor 1 so that perforations 7 in tube 6 can permit tube 6 to receive and collect materials at an equilibrium condition with other materials in pressure vessel 1, without disturbing the ongoing reaction pressure contained in pressure vessel 1.

After sufficient time for collecting materials in tube 6, crank 8 will be turned in an opposite direction and tube 6, containing material at equilibrium with other materials then in pressure vessel 1, can be withdrawn. Ball valves 2 and 3 may be closed and ball valve 3 may be removably attached from ball valve 2, permitting the sample in sealed tube 4 to be carried to a remote location for analysis.

The apparatus can be covered with sufficient insulation material, such as faced fiberglass batting or the like, to contain the temperatures of the sample materials. If desired, the apparatus containing withdrawn samples can be allowed to cool and later be reheated at the remote location for analysis thereby to establish the physical conditions of the samples existing when withdrawn from vessel 1.

What is claimed is:

1. A sampling apparatus for withdrawing and collecting samples from an operating pressure vessel without disturbing a reaction in said pressure vessel and while maintaining physical conditions of said sample, which apparatus comprises:
    (a) a pressure vessel having an aperture;
    (b) a first valve attached to said vessel and aligned with said aperture;
    (c) a first tube having a sealed end and an open end;
    (d) a second valve attached to said open end of said first tube and removably attached to said first valve;
    (e) a second tube coaxially oriented within said first tube, said second tube having a perforated end for receiving a sample from said vessel; and
    (f) means for sliding said perforated end of said second tube in and out of said second valve, said first valve, and said pressure vessel.

2. A sampling apparatus according to claim 1, wherein said means for sliding comprises a crank, a threaded rod attached at one end to said crank and extending into said first tube to contact threads in the end of said second tube, wherein said rod has the capability when rotated of urging said perforated end of said second tube in and out of said vessel.

3. A sampling apparatus according to claim 2, wherein said sliding means further comprises a longitudinal trough in said second tube and a guiding key protruding from the wall of said first tube into said longitudinal trough.

4. A sampling apparatus according to claim 2, wherein said sliding means further comprises a longitudinal trough in said first tube and a guiding key protruding from the wall of said first tube into said longitudinal trough.

5. A sampling apparatus according to claim 3, wherein said key can be located at a plurality of predetermined longitudinal distances along said first tube.

6. A sampling apparatus according to claim 5 having an external layer of thermal insulation.

7. A sampling apparatus according to claim 6, wherein said pressure vessel is capable of containing reaction mixtures at a pressure of at least 100–300 psi and at a temperature of at least 800° F.

8. A sampling apparatus according to claim 6, wherein said pressure vessel is capable of containing reaction mixtures at pressures in the range 0.0001–100 psi.

* * * * *